(12) United States Patent
Luebben

(10) Patent No.: US 9,290,462 B1
(45) Date of Patent: Mar. 22, 2016

(54) POLYTHIOL CURING AGENTS WITH LOW ODOR

(71) Applicant: TDA Research, Inc., Whet Ridge, CO (US)

(72) Inventor: Silvia DeVito Luebben, Golden, CO (US)

(73) Assignee: TDA Research, Inc., Wheat Ridge, CO (US)

( * ) Notice: Subject to any disclaimer, the term of this patent is extended or adjusted under 35 U.S.C. 154(b) by 0 days.

(21) Appl. No.: 14/574,385

(22) Filed: Dec. 17, 2014

Related U.S. Application Data

(60) Provisional application No. 61/917,261, filed on Dec. 17, 2013.

(51) Int. Cl.
| | |
|---|---|
| *C08G 59/00* | (2006.01) |
| *C07D 251/38* | (2006.01) |
| *C07C 323/34* | (2006.01) |
| *C08G 59/66* | (2006.01) |

(52) U.S. Cl.
CPC ............ *C07D 251/38* (2013.01); *C07C 323/34* (2013.01); *C08G 59/66* (2013.01)

(58) Field of Classification Search
CPC .................................................... C08K 5/3492
See application file for complete search history.

(56) References Cited

U.S. PATENT DOCUMENTS

| | | | |
|---|---|---|---|
| 3,505,166 | A | 4/1970 | Jones et al. |
| 3,624,160 | A | 11/1971 | Jones et al. |
| 3,828,100 | A | 8/1974 | Goss et al. |
| 3,873,502 | A | 3/1975 | Hickner et al. |
| 4,092,293 | A | 5/1978 | Harris et al. |
| 4,177,173 | A | 12/1979 | Carr |
| 4,626,562 | A | 12/1986 | Motomura et al. |
| 4,879,414 | A | 11/1989 | Johnson et al. |
| 4,927,902 | A | 5/1990 | Johnson et al. |
| 5,214,098 | A | 5/1993 | Setiabudi et al. |
| 5,430,112 | A | 7/1995 | Sakata et al. |
| 5,972,423 | A | 10/1999 | Abbey et al. |
| 6,153,719 | A | 11/2000 | Abbey et al. |
| 6,492,454 | B1 | 12/2002 | Ozawa et al. |
| 6,872,762 | B2 | 3/2005 | Burns et al. |
| 8,420,738 | B2 | 4/2013 | Nakano et al. |
| 2010/0273940 | A1 | 10/2010 | Urakawa et al. |

FOREIGN PATENT DOCUMENTS

| | | |
|---|---|---|
| EP | 2597047 | 5/2013 |
| JP | 05-093179 A | 4/1993 |
| WO | WO-2012059558 | 5/2012 |

*Primary Examiner* — Shane Fang
(74) *Attorney, Agent, or Firm* — Brian J. Elliott

(57) ABSTRACT

This invention relates to the composition of matter of polythiols having a chemical structure in FIG. 1. In certain embodiments this invention provides a polythiol with low or no odor and which is a liquid, a waxy solid or a semi-solid at 22° C. In another embodiment the polythiols have a viscosity lower than 100,000 cP at 50° C. In other embodiments, the invention provides a mixture of thiol compounds or a mixture of thiol and amine compounds.

6 Claims, 2 Drawing Sheets

POLYTHIOL CURING AGENTS WITH LOW ODOR

CROSS REFERENCE TO RELATED APPLICATIONS

The present application claims the benefit of the provisional application No. 61/917,261 filed Dec. 17, 2013 (titled POLYTHIOL CURING AGENTS WITH LOW ODOR, by Silvia DeVito Luebben, which is incorporated by reference herein. Provisional application No. 61/917,261 is not admitted to be prior art with respect to the present invention by its mention in the background or cross-reference section.

STATEMENT REGARDING FEDERALLY SPONSORED RESEARCH OR DEVELOPMENT

This invention was made using U.S. government funding through the Environmental Protection Agency contract No. EP-D-11-057 and the National Institute of Food and Agriculture contract No. 2013-33610-20834. The government has certain rights in this invention.

BACKGROUND

Polythiol compounds and resins are well known in art and have found applications as curing agents for epoxies, isocyanates and in thiol-ene chemical reactions. They also have found uses as additives in the rubber industry. Most polythiol curing agents are unpleasant to use because of the residual odor due to impurities and degradation products. Furthermore, most polythiol-cured epoxies cure to give products of low Young's modulus and high water uptake. Examples of commercially available polythiols are shown in FIG. 1.

When used to cure epoxies resins, polythiols have certain advantages over other curing agents such as polyamines because the cure kinetics of epoxies with polythiols is typically more easily controlled than that of epoxies with amines. The time required to reach full hardness can be shortened by increasing the catalyst load while still maintaining a sufficiently long pot-life. The epoxy/thiol reaction often exhibits an induction period during which the mixture of Parts A (epoxy resin) and B (hardener) remains fluid and workable followed by a sharp gelation period when curing commences with rapid development of the final mechanical properties. Thus, the cure kinetics of epoxy with thiol is often non-linear with time, beginning very slowly and then dramatically accelerating at a certain point in time (acceleration point). The acceleration point in a given system may be controlled by choice of catalyst and catalyst loading. Thus, thiol-cured epoxy resins can exhibit a much sharper gel transition than most of the other classes of epoxy hardeners especially at ambient and low temperatures. The initial low-viscosity phase of curing is often called the "application life" and is important in commercial applications to allow sufficient time to apply, cast and tool the product prior to the onset of gelation and hardening. Thiol-curing of epoxies is especially useful for curing at around ambient temperature (4-40° C.) and even at cold temperatures (−30-4° C.).

Curing of epoxy formulations with polythiol hardeners has been described for example by Harris (U.S. Pat. No. 4,092,293, 1978), Johnson (U.S. Pat. No. 4,879,414, 1989 and U.S. Pat. No. 4,927,902, 1990), Motomura (U.S. Pat. No. 4,626,562, 1986), Abbey (U.S. Pat. No. 5,972,423, 1999 and 6153719, 2000), Sakata (U.S. Pat. No. 5,430,112, 1995), Setiabudi (U.S. Pat. No. 5,214,098, 1993), Carr (U.S. Pat. No. 4,177,173, 1979), and Burns (U.S. Pat. No. 6,872,762 B2, 2005).

U.S. Pat. No. 4,092,293 relates to certain propoxylated ether polythiol curing agents for epoxy resins which are reported to impart hydrophobic characteristics to resultant thermoset polymers. This reference is incorporated by reference herein in its entirety for descriptions of epoxy resins, certain useful polythiol curing agents as well as methods of curing epoxy resins.

U.S. Pat. Nos. 4,879,414 and 4,927,902 relate to certain polythiol curing agents for epoxy resins prepared by the reaction of hydrogen sulfide or organic dithiols with polyglycidyl substituted amines. Exemplified curing agents have aromatic, methylene, bis-diphenyl, xylylene, cycloaliphatic, methylene bis-dicylohexyl, dimethylene cyclohexyl, methylene cyclohexyl or aliphatic cores with one or more thiol-substituted amine groups:

—N(CH$_2$CHOHCH$_2$SX)$_2$ where X is H or R'—SH, where R' is alkylene, cycloalkylene or alkylene substituted aromatic. The cured resins are reported to exhibit improved cured rates, better heat resistance, greater resistance to chemicals and greater resistance to water absorption. Each of these references is incorporated by reference herein in its entirety for descriptions of epoxy resins, certain useful polythiol curing agents as well as additives and methods of curing epoxy resins and applications of cured epoxy resins.

U.S. Pat. No. 4,626,562 relates to an epoxy resin composition consisting essentially of an epoxy compound having at least two epoxy groups in each molecule, certain esters of a mercaptoalkylcarboxylic acid and a tertiary amine-type curing accelerator. Certain polyol esters of mercaptoalkylcarboxylic are exemplified, such as triesters of trimethylolpropane. The epoxy composition is reported to be useful in construction and for repairs to asphalt concrete or cement concrete. This reference is incorporated by reference herein in its entirety for descriptions of epoxy resins, certain useful polythiol curing agents, catalysts and additives as well as methods of curing epoxy resins and applications of cured epoxies.

U.S. Pat. No. 5,972,423 relates to use of a curable filler composition including an epoxy compound, a polythiol and a catalyst for repairing substrate surfaces without need for application of a primer.

U.S. Pat. No. 6,153,719 relates to a composition useful as a sealer comprising certain epoxy compounds, a thiol curing agent, a catalyst and a phosphorous-containing compound having an ethylenically unsaturated group which is described as an adhesion-promoting compound. Each of these references is incorporated by reference herein for descriptions of epoxy resin materials that can be cured using polythiols, for descriptions of certain polythiol curing agents, useful catalysts and additives as well as for descriptions of methods of curing epoxies and applications of such epoxies.

U.S. Pat. No. 5,430,112 relates to epoxy resin compositions which contain certain epoxy resins, a polythiol and certain accelerators which are reported to exhibit curability at relatively low heating temperature and a long working life. Accelerators include a solid-dispersion-type amine adduct latent curing accelerator or an accelerator which is prepared by reaction of certain isocyanate compounds with certain primary of secondary amines. U.S. Pat. No. 5,214,098 relates to a hardenable mixture comprising an epoxide resin, a certain latent epoxide resin hardener, a certain amine and a certain thiol. U.S. Pat. No. 6,872,762 relates to a curable epoxy-based composition having an epoxy compound, a latent hardener, at least one solid organic acid and optionally a polythiol. Each of these references is incorporated by reference herein for descriptions of epoxy resin materials that can be cured using polythiols, for descriptions of certain polythiol curing agents and useful catalysts and particularly for useful latent catalysts (or accelerators) as well as for descriptions of additives and of methods of curing epoxies and applications of such epoxies.

U.S. Pat. No. 4,177,173 relates to polyepoxide curing employing a curing system having at least one polymercaptan and at least one catalyst which is a poly[(N,N-dimethylamino) alkyl ether. The combination of polymercaptan (polythiol) and poly amine catalyst is reported to provide rapid and effective curing. This patent reports that the pot life of thiol-cured epoxies can be extended as much as ten times by using a tertiary amine-ether catalyst alone or in combination with a traditional tertiary amine with no sacrifice in the cure rate once it commences (i.e. a sharp gel point is maintained). This reference is incorporated by reference herein in its entirety for descriptions of polyepoxies (epoxy resins), certain useful polythiol curing agents and particularly for certain useful amine catalysts (tertiary amine-ethers) for description of useful additives, as well as for method of curing epoxies.

Jones and coworkers report the use of certain tris(mercaptoalkyl)cyclohexanes as curing agents for epoxy resins (U.S. Pat. Nos. 3,505,166 and 3,624,160). The patents specifically report 1,2,4-tris(2-mercaptoethyl) cyclohexane and 1,3,5-tris (2-mercaptoethyl) cyclohexane.

Hickner et al. report the compositions of certain cycloaliphatic polythiols and their use as curing agents for polyepoxides (U.S. Pat. Nos. 3,873,502 and 3,828,100). The patent reports cycloaliphatic polythiols of formula:

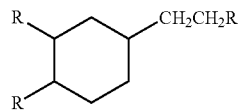

where R is —Cl, —Br, —SR$_1$SH or —OR$_2$SR$_1$SH and at least two R have a terminal thiol group, and R$_1$ is an alkylene group of 2 to 10 carbons having one or more —O— or —S— ether groups and R$_2$ is an alkylene group of 2-4 carbon atoms. Each of these patents is incorporated by reference herein for its description of cycloaliphatic polythiols including specific compounds of the listed formula.

Hiroshi reports an epoxy adhesive wherein the composition contains a triazinethiol containing at least one mercapto group (e.g. 1,3,5-trimercaptotriazine) (JP5093179(A), 1993).

U.S. published application 2010/0273940 relates to thiol curing agents for epoxy resins which is reported to have favorable pot life, good storage stability and where the cured product has good water resistance. The curing agent is described as containing a secondary or tertiary branched thiol compound having a substituent on a carbon atom at the alpha-position to a thiol group. Exemplified substituents on the alpha carbon are straight chain or branched alkyl groups. Specifically exemplified curing agents have formula:

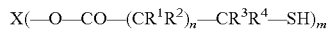

wherein n is an integer from 0 to 4 and m is an integer from 2 to 8, X is "an m valent aliphatic or aromatic residue of at most 20 carbon atoms which may have a substituent" and where R$^1$-R$^4$ are independently hydrogen, or an alkyl group having 1-10 carbon atoms and at least one of R$^3$ or R$^4$ is an alkyl group having 1-10 carbon atoms.

Burns (WO 2012059558 A1, 2011) teaches the use of polythiols having at least one secondary or tertiary thiol group per molecule; and a stabilizing component comprising a solid organic acid.

Kazuo (EP 2597047 A1), Nakano (U.S. Pat. No. 8,420,738 B2) and Ozawa (U.S. Pat. No. 6,492,454 B1) teach certain bismercaptotriazines as vulcanizing agents for rubbers with structure:

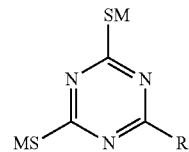

wherein M is H, Li, Na, K, ½ Mg, ½ Ca, ½ Ba and R is SH, OR$_1$, SR$_2$, NHR$_3$, NR$_4$R$_5$ and R$_1$, R$_2$, R$_3$, R$_4$ and R$_5$ are alkyl, alkenyl, aryl, aralkyl, alkylaryl, or cycloalkyl.

BRIEF SUMMARY OF THE INVENTION

Most current commercial liquid or waxy polythiol curing agents have a strong odor because of byproducts of synthesis. In contrast, 2,4,6-trimercaptotrizine has no odor at room temperature and can be used to cure epoxies, however it is a crystalline solid at room temperature, which makes its handling more challenging. This invention provides the composition of novel polythiol curing agents that are liquids, viscous liquids, and waxy solids semi-solids and also have no or low odor.

Polythiols of this invention have structures A, B and C in Scheme 1:

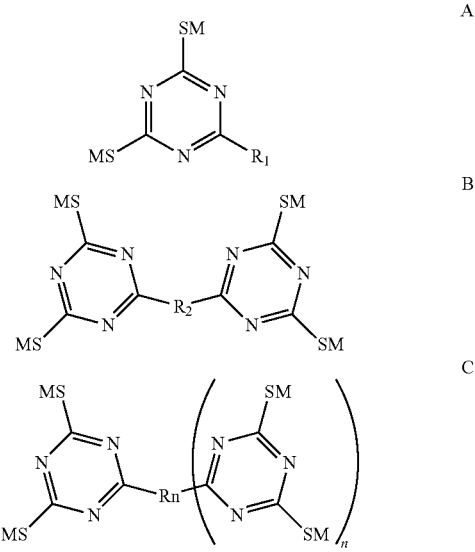

Wherein: M is selected from the group consisting of H, Li, Na, K, ½ Mg, ½ Ca, and ½ Ba; R$_1$ is a monovalent organic radical selected from the group of: —SR$_3$, —NHR$_3$, —N(R$_3$)$_2$, and —R$_3$; each R$_3$, independently from each other, is selected from the group consisting of a linear or branched alkyl group with 5 or more carbon atoms, an alkenyl group, an alkynyl group, a hydroxyalkyl group, a 2-hydroalkyl group, an aminoalkyl group, an arylalkyl group, an alkylaryl group, an alkoxylaryl group, an alkoxy group (RO—), an acyl group (R(C=O)—), a thioacyl group (R(C=S)—), alkylamino carbonyl group (RNH(C=O)—), an alkylaminothiocarbonyl group (RNH(C=S)—), an alkoxythiocarbonyl group (RO(C=S)—), and an alkoxycarbonyl group (RO(C=S)—); $R_2$ is bivalent organic radical selected from the group consisting of —S—, —S—S— —NH—, —$NR_3$—, —O—, —$R_4$—, —S—$R_4$—S—, —O—$R_4$—O—, —NH—$R_4$—NH—, —$NR_3$—$R_4$—NH—, —$NR_3$—$R_4$—$NR_3$—, —S—$R_4$—O—, -, —S—$R_4$—NH—, —O—$R_4$—NH—, —S—$R_4$—$NR_3$— and —O—$R_4$—$NR_3$—, wherein $R_4$ is a divalent organic radical as defined herein; $R_n$ is a multivalent organic radical; and "n" is an integer number from 3 to 6 $R_1$, $R_2$, $R_3$, $R_4$, $R_n$, may be oligomeric or polymeric in nature, i.e. may contain repeating units of monomers such as glycols, ethylene glycol, propylene glycol, ethers, fluoroethers, olefins, fluoroolefines, acrylates and methacrylates, vinyl compounds, alkynes, esters, amino acids, lactones and lactames, polyols, urethanes, epoxies, hydroxacids, dienes, polyenes, chloroolefines, diols, diamantes, polyamines. $R_1$, $R_2$, $R_3$, $R_4$, $R_n$ may optionally be substituted with a functional group or another organic radical as defined herein.

In preferred polythiols M is hydrogen.

Preferred polythiols are liquids, viscous liquids, waxy solid or semisolid at room temperature.

One embodiment of the invention is a polythiol comprising the chemical structure:

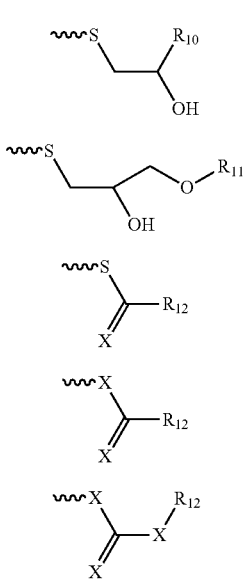

wherein $R_1$ is selected from the group consisting of: A), B), C), D), E), F) and G):

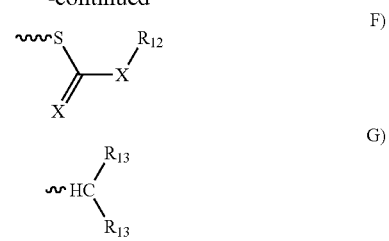

wherein $R_{10}$, $R_{11}$, $R_{12}$, and $R_{13}$ are selected from the group consisting of a hydrogen, a linear or branched alkyl group, an alkenyl group, an alkynyl group, a hydroxyalkyl group, an arylalkyl group, an alkylaryl group, an alkoxyaryl group, an acyl group (R(C=O)—), a thioacyl group (R(C=S)—), an alkylamino carbonyl group (RNH(C=O)—), an alkylaminothiocarbonyl group (RNH(C=S)—), an alkoxythiocarbonyl group (RO(C=S)—), and an alkoxycarbonyl group (RO(C=S)—), and wherein $R_{10}$, $R_{11}$, $R_{12}$, and $R_{13}$ may optionally be substituted with one or more organic functional groups; and wherein X is selected from the group of O, S, NH and NR, wherein R is a monovalent organic radical. In a further embodiment, the groups $R_{10}$, $R_{11}$, $R_{12}$, and $R_{13}$ are oligomeric or polymeric in nature, i.e. may contain repeating units of monomers such as glycols, ethylene glycol, propylene glycol, ethers, fluoroethers, olefins, fluoroolefines, acrylates and methacrylates, vinyl compounds, alkynes, esters, amino acids, lactones and lactames, polyols, urethanes, epoxies, hydroxacids, dienes, polyenes, chloroolefines, diols, diamines, polyamines and may optionally be terminated by a hydrogen, a linear or branched alkyl group, an alkenyl group, an alkynyl group, a hydroxyalkyl group, an arylalkyl group, an alkylaryl group, and an alkoxyaryl group, an acyl group (R(C=O)—), a thioacyl group (R(C=S)—), alkylamino carbonyl group (RNH(C=O)—), an alkylaminothiocarbonyl group (RNH(C=S)—), an alkoxythiocarbonyl group (RO(C=S)—), and an alkoxycarbonyl group (RO(C=S)—).

Another embodiment is a polythiol comprising the chemical structure:

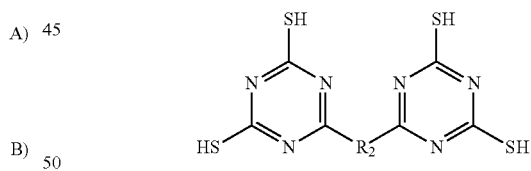

wherein $R_2$ is selected from the group consisting of —S—, —S—S— —NH—, —$NR_3$—, —O—, —$R_4$—, —S—$R_4$—S—, —O—$R_4$—O—, —NH—$R_4$—NH—, —$NR_3$—$R_4$—NH—, —$NR_3$—$R_4$—$NR_3$—, —S—$R_4$—O—, -, —S—$R_4$—NH—, —O—$R_4$—NH—, —S—$R_4$—$NR_3$— and —O—$R_4$—$NR_3$—; wherein $R_3$ is a monovalent organic radical and $R_4$ is a divalent organic radical; and $R_3$ and $R_4$ may optionally be substituted with one or more organic functional groups. In a further embodiment the $R_4$ has an oligomeric or polymeric structure and comprises monomer repeat units selected from the group consisting of glycols, ethylene glycol, propylene glycol, ethers, fluoroethers, olefins, fluoroolefines, acrylates and methacrylates, vinyl compounds, alkynes, esters, amino acids, lactones and lactames, polyols, urethanes, epoxies, hydroxacids, dienes, polyenes, chloroolefines, diols, diamines, and polyamines.

Another embodiment is a polythiol comprising the chemical structure:

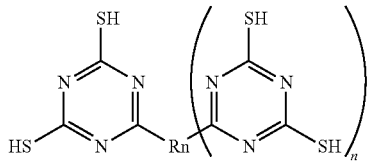

wherein Rn is a multivalent organic radical, and "n" is an integer equal to or greater than 2, and Rn may optionally be substituted with one or more organic functional groups. In a further embodiment $R_n$, is an oligomer or a polymer comprising monomer repeating units selected from the group consisting of glycols, ethylene glycol, propylene glycol, ethers, fluoroethers, olefins, fluoroolefines, acrylates, methacrylates, vinyl compounds, alkynes, esters, amino acids, lactones, lactames, polyols, urethanes, epoxies, hydroxacids, dienes, polyenes, chloroolefines, diols, diamines and polyamines.

A further embodiment of any of the three independent embodiments above is a polythiol which is a liquid, a waxy solid or a semi-solid at 22° C.

A further embodiment of any of the three independent embodiments above is a polythiol which has a viscosity lower than 100,000 cP at 50° C.

Another embodiment is a mixture of thiol compounds comprising at least one of the polythiols as in any one of the above embodiments.

Another embodiment is a mixture of thiol and amine compounds comprising at least one of the polythiols as in any one of the above embodiments.

In a preferred embodiment, the polythiol has the structure:

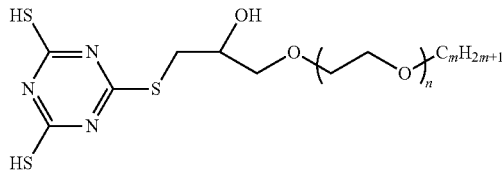

Wherein n is an integer number from 2 to 30 and m is an integer number from 1 to 20.

In another preferred embodiment the polythiol has the structure:

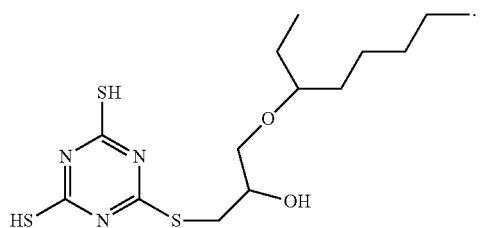 [SMILES: CCCCCC(CC)OCC(O)CSc1nc(S)nc(S)n1]

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Figure 1:
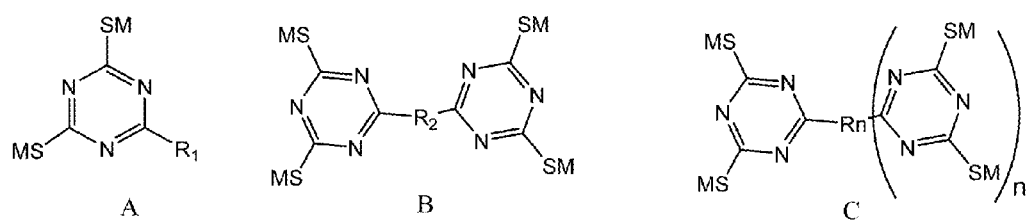
FIG. 1 shows examples of polythiols of the present invention.
Figure 2:
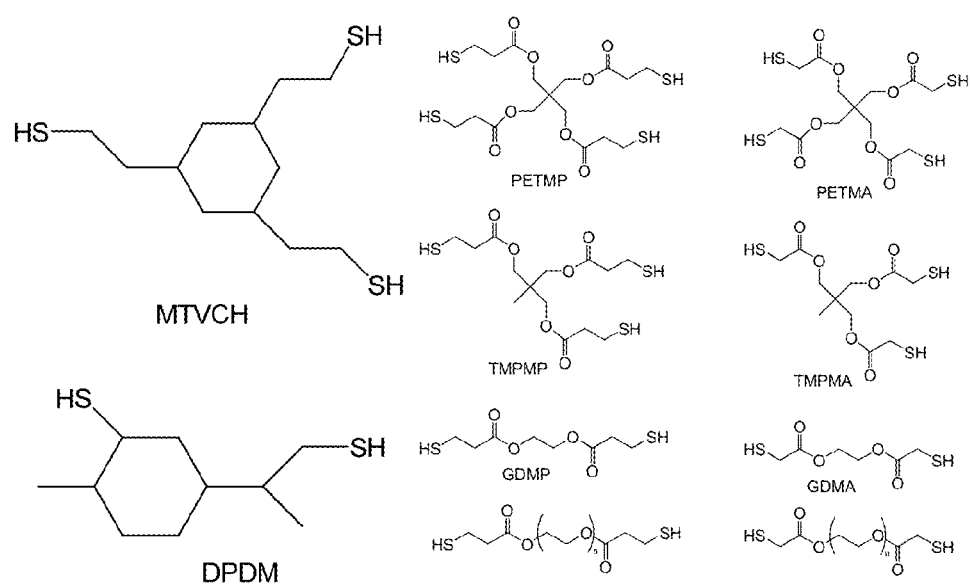
FIG. 2 shows examples of commercially available polythiols.

A thiol or mercaptan is a compound carrying one or more SH groups. A polythiol, or a polymercaptan, is a compound or a mixture of compounds with average number of SH groups per molecule higher than 1, preferably higher than 1.5. More preferred polythiols have two or more SH groups per molecule. Polythiols may be non-polymeric compounds or polymeric compounds, wherein the SH groups terminate the polymer chain or are pendant groups along the polymer chain. A polythiol mixture may further comprise one or more monothiol compounds with a single SH per molecule. Typically this component is used to lower the viscosity of the mixture and does not contribute to cross-linking during cure.

The thiol equivalent weight of a polythiol is the weight of material in grams which contains one gram-equivalent of SH groups.

The polythiols of the present invention may also exist as a thiol salt or a polythiol salt.

The structure of the polythiols of this invention are shown in Scheme 1, wherein, M is selected from the group consisting of H, Li, Na, K, ½ Mg, ½ Ca, and ½ Ba; $R_1$ is a monovalent organic radical selected from the group of: —$SR_3$, —$NHR_3$, —$N(R_3)_2$, and —$R_3$; each $R_3$, independently from each other, is selected from the group consisting of a linear or branched alkyl group with 5 or more carbon atoms, an alkenyl group, an alkynyl group, a hydroxyalkyl group, a 2-hydroalkyl group, an aminoalkyl group, an arylalkyl group, an alkylaryl group, an alkoxylaryl group, an alkoxy group (ROA an acyl group (R(C=O)—), a thioacyl group (R(C=S)—), alkylamino carbonyl group (RNH(C=O)—), an alkylaminothiocarbonyl group (RNH(C=S)—), an alkoxythiocarbonyl group (RO(C=S)—), and an alkoxycarbonyl group (RO(C=S)—); $R_2$ is bivalent organic radical selected from the group consisting of —S—, —S—S— —NH—, —$NR_3$—, —O—, —$R_4$—, —S—$R_4$—S—, —O—$R_4$—O—, —NH—$R_4$—NH—, —$NR_3$—$R_4$—NH—, —$NR_3$—$R_4$—$NR_3$—, —S—$R_4$—O—, -, —S—$R_4$—NH—, —O—$R_4$—NH—, —S—$R_4$—$NR_3$— and —O—$R_4$—$NR_3$—, wherein $R_4$ is a divalent organic radical as defined herein; $R_n$ is a multivalent organic radical; and "n" is an integer number from 3 to 6 $R_1$, $R_2$, $R_3$, $R_4$, $R_n$, may be oligomeric or polymeric in nature, i.e. may contain repeating units of monomers such as glycols, ethylene glycol, propylene glycol, ethers, fluoroethers, olefins, fluoroolefines, acrylates and methacrylates, vinyl compounds, alkynes, esters, amino acids, lactones and lactames, polyols, urethanes, epoxies, hydroxacids, dienes, polyenes, chloroolefines, diols, diamantes, polyamines. $R_1$, $R_2$, $R_3$, $R_4$, $R_n$ may optionally be substituted with a functional group or another organic radical as defined herein.

Chemical terms used herein are generally as used in the art and intended to have their broadest meaning as used in the art.

A monovalent organic radical (or simply a monovalent radical) is a group of atoms (molecular fragment) derived formally by removal of a single hydrogen atom from an organic molecule. Examples of monovalent organic radicals include, among others, $CH_3$— (methyl radical), $CH_3$—$CH_2$—, HO—$CH_2$—$CH_2$—, $C_6H_5$—$CH_2$—, and $CH_3$—CH=CH—. Additional organic radicals are species derived formally by removal of a single hydrogen atom from a non-carbon atom (e.g., O, N, S) in the organic molecule, such as alkoxide radicals (R—O—, where R is an alkyl or other organic group) which is derived by removal of hydrogen from an alcohol or an amine radical (RR'—N—, where one of R or R' is an alkyl or other organic group A divalent organic radical (or simply a divalent radical) is a group of atoms (molecular fragment) derived formally by removal of two hydrogen atoms from an organic molecule where both hydrogens may be removed from the same atom in the organic molecule or two different atoms in the organic molecule. The hydrogen atoms may be formally removed from a carbon atom or heteroatom. Exemplary divalent organic radicals are: —$CR_2$—, —$CF_2$—, —$C_6R_4$— (a phenylene radical), —$(CR_2)_n$—, —$(CR_2)_n$—X—$(CR_2)_m$—, —X—$(CH_2)$—, —NR"—, where n and m are integers, each R, independent of other R's is hydrogen, halogen, alkyl or other organic group, R" is an organic group and X is O, S, NR, CO, CS, NRCO, COO, double bond, triple bond, or phenylene, among others. Other examples of divalent organic radicals includes (a) aromatic hydrocarbon radicals having from 6 to about 20 carbon atoms and halogenated derivatives thereof, (b) alkylene radicals and cycloalkylene radicals having from 2 to about 20 carbon atoms, $C_{(2-8)}$ alkylene terminated polydiorganosiloxane.

A multivalent organic radical (or simply a multivalent radical) is a group of atoms (molecular fragment) derived formally by removal of three or more hydrogen atoms from an organic molecule. Examples of multivalent radicals include —(R)C<, —$(CR_2)_n$—CR<, —$(CR_2)_n$—X<, —$(CR_2)_n$—X(-)—$(CR_2)_m$—Y—, —$(CR_2)_n$—X(-)—$(CR_2)_m$—, where n and m are integers, each R, independent of other R's is hydrogen, halogen, alkyl or other organic group, X is N, CR, N—CO, and Y is $CR_2$, CO, COO, CS, O, S, NR, NR—CO, and phenyl ($C_8R_4$).

Organic radicals can contain linear or branched carbon chains or rings containing carbon and other atoms (e.g., O, S, N). Organic radicals can contain double bonded carbons, triple bonded carbons, non-aromatic or aromatic rings. Organic radical may be aliphatic, alicyclic or aromatic. An aliphatic organic radical results from removal of one or more hydrogen atoms from a saturated or unsaturated carbon compounds, in which the carbon atoms are joined in open chains. An alicyclic organic radical results from removal of one or more hydrogen atoms from a saturated or partially unsaturated cyclic carbon compound, an aromatic radical results from removal of one or more hydrogen atoms from an aromatic organic molecule. Carbons in organic radicals can be substituted with one or more various non-hydrogen substituents, including halogens, amino group, alkoxide or hydroxide groups, alkyl thiols or thiols, oxygen or sulfur (to form CO or CS groups).

An organic radical may be derived from the formal removal of one or more hydrogen atoms from an oligomeric, pre-polymeric or polymeric species. The one or more hydrogen atoms may be formally removed from the end of the polymer chain or along its length. Oligomeric, pre-polymeric or polymeric species include polyglycols, polyethers, poly(fluoroethers), polyglycols, polyacetals, polyolefins, polystyrene and its copolymers, polyfluoroolefins, polyoxides, polychloroolefins, polychlorofluoroolefins, polysiloxanes, polyesters, polybromoesters, natural and synthetic rubbers (vulcanized or un-vulcanized), polyacids, polycarbonates, polyanhydrides, polysulfides, polyamides, polyamines, polyimides, vinyl polymers and polymers derived from the polymerization of unsaturated monomers, polyacrylates and polymethacrylates, polyacrylonitriles and its copolymers, polybutadiene and its copolymers, alkyds, polyalcohols, polyurethanes, epoxies, cellulose and its derivatives, starch and its derivatives, other natural occurring polymers, polypeptides, and other biomolecules and their combinations and copolymers. The molecular weight of preferred oligomeric, pre-polymeric or polymeric species ranges from 10-10,000 Dalton and more preferable from 200 to 3000 Dalton.

An organic radical may optionally be substituted with a functional group or another organic radical.

A functional group is a combination of atoms (or in the case of halides a single atom) that when attached to an organic radical has either a specific reactivity or imparts to the molecule a specific character, for example, by electron withdrawing or electron donating action. Hydrogen is not a functional group. Typical functional groups include halogen atoms, nitro groups, cyano groups, cyanate groups, thiocyanate groups, isocyanate groups, thioisocyanate groups, alcohol groups (e.g. organic groups with one or more OH groups), polyol groups (e.g., organic groups with more than one and more typically a plurality of OH groups), alkoxide groups, ether groups (e.g., alkyl or other organic groups containing one or more C—O—C linkages), thiols, thioether groups (e.g., alkyl or other organic groups containing one or more C—S—C linkages), silyl (e.g., $R_3Si$—, where R is various substituents or organic groups), siloxy (e.g., $R_2$—Si(OR)—), aldehyde groups (organic radicals containing a —COH moiety), ketone groups (organic radicals containing a CO moiety), carboxylic acids (organic radicals containing —COOH groups or —COO$^-$ groups, carboxylic ester groups (organic groups containing —COOR" groups, where R" is an alkyl group or other organic group), acyl halide groups (organic groups containing —COX groups where X is a halide), anhydride groups (an organic group containing an anhydride group), groups containing other carboxylic acid derivatives, amino groups, alkyl amino groups, amino oxide groups and groups containing other derivatives of amino groups, diazo groups, azide groups, phosphoric acid ester groups, alkyl phosphate groups and groups containing other phosphoric acid derivatives, phosphinic acid groups, and groups containing phosphinic acid derivatives, phosphine groups, groups containing phosphonium salts, sulfuric acid ester groups, sulfate groups, sulfonate groups, groups containing sulfinic acid derivatives, groups containing sulfonium salts, groups containing oxonium salts, groups containing carbon-carbon double bonds (e.g., alkenyl groups) and groups containing carbon-carbon triple bonds (e.g., alkynyl groups), and combinations thereof. Functional groups include organic functional groups. Many other functional groups are known in the art. Aldehyde groups, halogen atoms, isocyanate groups and acyl halide groups are examples, among many others, of functional groups that may be used to impart a desired reactivity to a molecule or polymer. Nitro groups, cyano groups, chlorine and bromine atoms, and carboxylic acid derivatives are examples, among many others, of functional groups with electron-withdrawing properties. Alcohol groups, alkoxide groups, thiol groups, mercapto groups, and amino groups are examples, among many others, of groups with electro-donating properties. The terms "electron-withdrawing group: and "electron-donating group" are terms that are well known in the art of chemistry. Many groups are known in the art which are classified into one of these groupings. These terms are used herein to have their broadest meaning in the art. One of ordinary skill in the art understands the meaning of these terms and knows how to select functional groups which will function as an electron-withdrawing group or an electron-donating group in a particular molecular structure.

The terms alkyl or alkyl group refer to a monoradical of a straight-chain or branched saturated hydrocarbon and to cycloalkyl groups having one or more rings. Alkyl groups may include portions that are straight-chain, branched or cyclic. Unless otherwise indicated alkyl groups have 1-20 carbon atoms (C1-C20 alkyl groups) and preferred are those that contain 1-12 carbon atoms (C1-C12 alkyl groups). In specific embodiments, alkyl groups contain 1 to 3 carbon atoms (C1-C3 alkyl groups). Specific linear and branched alkyl groups include, by way of example, methyl, ethyl, n-propyl, i-propyl, n-butyl, i-butyl, s-butyl, t-pentyl, hexyl groups, heptyl groups, octyl groups, nonyl groups and decyl groups, including all isomers thereof. The term cycloalkyl refers to cyclic alkyl groups having 3 to 20 carbon atoms (C3-C20 cycloalkyl group) having a single ring or multiple rings, including bicyclic, tricyclic, fused or spiro ring structures. Cycloalkyl groups also include those having linked cycloalkyl rings, such as those linked by a single bond or a methylene (e.g., bicyclohexane, or biscyclohexylmethylene) or those linked by an atom or group, such as —O—, —S—, —CO—, or —NR—, where R is hydrogen or a C1-C6 alkyl. Cycloalkyl groups include, by way of example, cyclopropyl, cyclobutyl, cyclopentyl, cyclohexyl, cylcoheptyl, cyclooctyl, and the like, or multiple ring structures such as adamantany. Unless otherwise indicated alkyl groups including cycloalkyl groups are optionally substituted as defined herein. In specific embodiments, alkyl groups are haloalkyl groups substituted with one or more halogens, particularly F, CI or Br, which include perhalogenated alkyl groups where all hydrogens of an alkyl group are replaced with a halogen. Haloalkyl groups include among others, trifluoromethyl, pentafluoroethyl, trichloromethyl, 2,2,2-trihaloethyl, 2,2 dihalopropyl, 4-halocyclohexyl, etc. In specific embodiments, alkyl groups are substituted with one or more hydroxy groups. Hydroxyalkyl groups include those substituted with 1-6 hydroxy groups. Hydroxyl alkyl groups include among others, hydroxymethyl, 2-hydroxyethyl, 2,3-dihydroxypropyl, 4-hydroxycyclohexyl, etc.

Arylalkyl, heterocyclylalkyl or heteroaryl are a subset of substitued alkyl groups and alkyl refer respectively to alkyl groups, substituted with an aryl, heterocyclyl or heteroaryl groups. All of which groups are as defined herein. Specific arylalkyl groups include benzyl, phenethyl (generally phenalkyl), morpholinylalkyl, pyridinylalkyl.

The terms alkenyl or alkenyl group refer to a monoradical of a straight-chain, branched or cyclic hydrocarbon group (cycloalkenyl) having one or more double bonds. Alkenyl groups may include straight-chain, branched and/or cyclic portions. Cycloalkenyl groups have one or more rings wherein at least one ring contains a double bond. Unless otherwise indicated alkenyl groups have 2 to 20 carbon atoms and more specifically contain 2-12 carbon atoms. Alkenyl groups may contain one or more double bonds (C=C) which may be conjugated or unconjugated. Preferred alkenyl groups are those having 1 or 2 double bonds and include omega-alkenyl groups. Alkenyl groups include those having 2 to 6 carbon atoms including ethylene (vinyl), propylene, butylene, pentylene, and hexylene groups including all isomers thereof. Cycloalkenyl groups include, by way of example, single ring structures (monocyclic) such as cyclopropenyl, cyclobutenyl, cyclopentenyl, cyclohexenyl, cyclooctenyl, cylcooctadienyl and cyclooctatrienyl as well as multiple ring structures (bicylic, tricyclic, spiro or linked rings). Unless otherwise indicated alkenyl groups including cycloalkenyl groups are optionally substituted.

The terms alkynyl or alkynyl group refers to a monoradical of an unsaturated straight-chain, branched or cyclic hydrocarbon having one or more triple bonds (CC). An alkynyl group may have portions that are straight-chain, branched and/or cyclic. Unless otherwise indicated alkynyl groups have 2 to 20 carbon atoms and more specifically contain 2-12 carbon atoms. Alkynyl groups include ethynyl, propargyl, and the like. In specific embodiments, alkynyl groups have 2-6 carbon atoms. Unless otherwise specified alkynyl groups are optionally substituted as defined herein.

Aromatic ring refers to one or more conjugated ring (s) in which p orbitals of the ring atoms are delocalized or conjugated over the ring(s). Aromatic rings may contain one or more heteroatoms. In specific embodiments, heteroatoms are N, O or S. An aromatic ring may be a single ring, e.g., a 5- or 6-member ring, or two or more fused rings, e.g., two or three 6-member rings or one or two 5-member rings fused to one or two six-member rings.

An aromatic group or aryl group is a group containing at least one aromatic ring. The group is formally derived by removing a hydrogen from a ring atom. A heteroaromatic group or heteroaryl group is a group containing at least on aromatic ring containing at least one heteroatom. Rings of aryl or heteroaryl groups may be linked by a single bond or a linker group or may be fused. Exemplary aryl groups include phenyl, biphenyl and naphthyl groups. Aryl and heteroaryl groups include those having from 6 to 20 carbon atoms and those containing 6-12 carbon atoms. Unless otherwise noted aryl and heteroaryl groups are optionally substituted as described herein. In specific embodiments herein aryl groups include those in which all ring atoms are carbon. In specific embodiments aryl and heteroaryl groups are those having one, two or three rings of which at least one is aromatic. In specific embodiments, aryl and heteroaryl groups have 6-12 ring atoms of which 1-6 and more specifically 1-4 are heteroatoms, particularly N, O or S.

The term "alicyclyl" generically refers to a monoradical that contains one or more rings of carbon atoms and heteroatoms, which may be a saturated ring (e.g., cyclohexyl) or unsaturated (e.g., cyclohexenyl), but which are not aromatic. More specifically alicyclic groups contain 3-20 ring atoms which can all be carbons or of which 1-8 ring atoms can be heteroatoms. In specific embodiments, heteroatoms include O, N, S, P or B. In specific embodiments, heteroatoms are O, N and S. Ring structures have three or more atoms and typically have 3-12 atoms. Rings structures may be fused or linked. Ring structures may be for example bicylic, or tricyclic. Rings may be linked with a single bond, a methylene, alkylene or other specified linking groups. Heterocyclyl is a subset of alicyclyl which refers to a monoradical that contains at least one ring of atoms, which may be a saturated, or unsaturated wherein one or more carbons of the ring are replaced with a heteroatom (a non-carbon atom) To satisfy valence any heteroatoms may be bonded to H or a substituent groups. One or more ring carbons of alicyclyl and heterocyclyl groups may optionally be replaced with —CO— or —CS— groups. Alicyclyl and hererocyclyl groups are optionally substitued as defined herein. In specific embodiments, alicyclyl and heterocyclyl groups contain 6-12 carbons, optionally contain 1-4 heteroatoms, optionally contain one or two double bonds, and/or optionally replace one or two ring carbons with —CO— or —CS— groups.

Heteroatoms include among others, O, S, N, P, B, Si, As, Bi, Ge, Sn, and Sb. In more specific embodiments, heteroatoms include O, N, S, P or B. In specific embodiments, one or more heteroatoms are substituted for carbons in aromatic or carbocyclic rings.

To satisfy valence any heteroatoms in such aromatic or carbocyclic rings may be bonded to H or a substituent group.

Alkoxy refers generally to groups of structure —OR where R is an alkyl group as defined herein. In specific embodiments, alkoxy groups have 1-6 or 1-3 carbon atoms. Specific examples include methoxy-, ethoxy-, propoxy-, isopropoxy-, cyclopropyloxy-, cyclohexyloxy- and the like. Alkenoxy and alkynoxy refer similarly to groups —OR, where R is an alkenyl group or alkynyl group, respectively, as defined herein. In specific embodiments, alkenoxy and alkynoxy groups have 2-8 or 2-4 carbon atoms. Aryloxy, heteroaryloxy, heterocyclyloxy and similar terms refer to groups —OR where the R is an aryl, heteroaryl, heterocyclyl or similar group, respectively, as defined herein. Specific aryloxy groups include phenyloxy, biphenyloxy. Alkoxy groups are optionally substituted as described herein.

Alkoxyalkyl, alkoxyalkenyl, alkoxyalkynyl are subsets of substituted alkyl, alkenyl or alkynyl groups and refer respectively to alkoxy substituted alkyl, alkenyl or alkynyl groups. All of which groups are as defined herein and all of which groups are optionally substituted as defined herein.

Arylalkyl, heterocyclylalkyl or heteroaryl are a subset of substituted alkyl groups and alkyl refer respectively to alkyl groups, substituted with an aryl, heterocyclyl or heteroaryl groups. All of which groups are as defined herein. Specific arylalkyl groups include benzyl, phenethyl (generally phenalkyl), morpholinylalkyl, pyridinylalkyl. Arylalkyl, heterocyclylalkyl or heteroaryl groups are optionally substituted as defined herein.

Acyl refers generally to groups of structure —COR, where R is hydrogen (a formyl group) or an aliphatic or aromatic group, which includes alicylic, heterocyclic, aromatic or heteroaromatic groups. In specific embodiments, acyl groups have 1-20, 1-12 or 1-6 carbon atoms and optionally 1-3 heteroatom, optionally one double bond or one triple bond. In specific embodiments, R is a C1-C6 alkyl, alkenyl or alkynyl group. cyclic configuration or a combination thereof, attached to the parent structure through a carbonyl functionality. Examples include acetyl, benzoyl, propionyl, isobutyryl, or oxalyl. The R group of acyl groups is optionally substituted as described herein.

The term amino group refers generally to a —N(R)$_2$ group where each R independently is hydrogen, alkyl, alkenyl, alkynyl, alicyclyl, heterocyclyl, aryl or heteroaryl each of which is optionally substituted as defined herein and where named groups are as defined herein. In specific embodiments, an amino group is —NH$_2$ or an alkylamino, wherein one or both of the R groups are optionally substituted alkyl groups and the other R is hydrogen or a bisalkylamino group where both of the R groups are optionally substituted alkyl groups. In a specific embodiment, one or both of the R groups are aryl groups and the other of R is a hydrogen. More specifically R groups include optionally substituted C1-C6 alkyl groups, unsubstituted C1-C6 alkyl groups, haloalkyl groups, and hydroxyalkyl groups and aryl substituted alkyl groups. Specific aryl groups include optionally substituted phenyl groups and halogen substituted phenyl groups.

The term oxo group and thioxo group refer to substitution of a carbon atom with a =O or a =S to form respectively —CO (carbonyl) or —CS— (thiocarbonyl) groups.

The term mercapto refers to a —SH group.

Optional substitution herein most generally includes substitution by one or more halogen, hydroxy group, nitro group, cyano group, isocyano group, oxo group, thioxo group, azide group, cyanate group, isocyanate group, nitroso group, phosphine group, phosphate group, thiocyano group, thiocyanate group, —COR$_6$ group, —COOR$_6$ group, CON(R$_6$)$_2$ group, —CSR$_6$ group, —CS—OR$_6$ group, —N(R$_6$)$_2$ group, —CO—O—CO—R$_6$, —CO—NR$_6$—CO—R$_6$, —N=C (R$_6$)$_2$, —CR$_6$=NR$_6$, alkyl group, alkenyl group, alkynyl group, alkoxy group, alkoxyalkyl group, alkoxyalkenyl group, alkoxyalkynyl group, haloalkyl, haloalkenyl, haloalkynyl, or haloalkoxy, where each R$_6$ is independently, a hydrogen, an alkyl, alkenyl, alkynyl, or aryl group, each of which R$_6$ or substituent group is, if possible, optionally substituted with one or more halogen, hydroxy group, nitro group, cyano group, isocyano group, oxo group, thioxo group, azide group, cyanate group, isocyanate group, nitroso group, phosphine group, phosphate group, thiocyano group, thiocyanate group, unsubstituted alkyl, unsubstituted alkenyl, unsubstituted alkynyl, or unsubstituted aryl groups. In specific embodiments, alkyl groups are C1-C3 alkyl groups. In specific embodiments, alkyl groups are unsubstituted C1-C3 alkyl groups. In specific embodiments, alkyl and alkenyl groups are cycloalkyl or cycloalkenyl groups, respectively, having 3-8 carbon ring atoms and which are in turn optionally substituted. In specific embodiments, aryl groups are groups having 1 or 2 5- or 6-member rings at least one of which is aromatic and which optionally has 1-4 heteroatoms, particularly heteroatoms selected from N, O or S. In specific embodiments, aryl groups are carbocyclic groups having no heteroatoms. In specific embodiments, aryl groups are carbocyclic unsubstituted groups or are unsubstituted heteroaryl groups. In specific embodiments, optional substitution is substitution with 1-12 non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substituents contain 6 or fewer carbon atoms. In specific embodiments, optional substitution is substitution by one or more halogen, hydroxy group, cyano group, oxo group, thioxo group, unsubstituted C1-C6 alkyl group or unsubstituted aryl group.

As to any of the groups herein which contain one or more substituents, it is understood, that such groups do not contain any substitution or substitution patterns which are sterically impractical and/or synthetically non-feasible. In addition, the compounds of this invention include all stereochemical and optical isomers arising from optional substitution as defined herein.

Preferred polythiols of this invention is those with structures A, B, or C in Scheme 1 Wherein M is hydrogen.

Preferred polythiol curing agents of this invention have the structure:

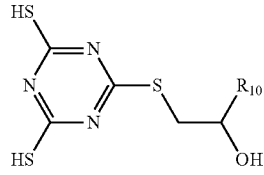

Wherein R$_{10}$ is a monovalent organic radical. Preferred R$_{10}$ is selected from the group consisting of hydrogen, a linear or branched alkyl group, an alkenyl group, an alkynyl group, a hydroxyalkyl group, an arylalkyl group, an alkylaryl group, and an alkoxylaryl group.

More preferred compounds have structure:

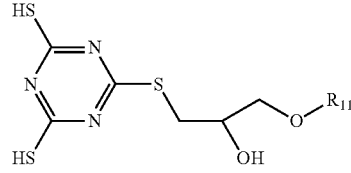

Wherein R$_{11}$ is hydrogen, a linear or branched alkyl, alkenyl, aryl, aralkyl, alkylaryl, or cycloalkyl, acyl, thioacyl, or is oligomeric or polymeric in nature, i.e. contains repeating units of monomers such as glycols, ethylene glycol, propylene glycol, ethers, fluoroethers, olefins, fluoroolefines, acrylates and methacrylates, vinyl compounds, alkynes, esters, amino acids, lactones and lactames, polyols, urethanes, epoxies, hydroxacids, dienes, polyenes, chloroolefines, diols, diamines, polyamines. R$_{11}$ may optionally be substituted with a functional group or another organic radical as defined herein.

In one embodiment most preferred R$_{11}$ is a linear or branched C$_5$-C$_{20}$ alkyl group, An example of one of the most preferred compounds is:

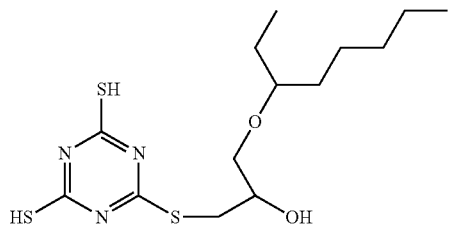

In another embodiment R$_{11}$ is a C$_1$-C$_{20}$ alkyl-terminated polyglycol oligomer.

An example of this is

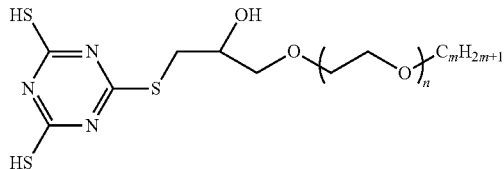

Wherein n is an integer number selected from 2-30 and m is an integer number selected from 1-20.

Preferably, n is an integer number selected from 4-10 and m is either 8, 10, 12, 14, or 16.

Other preferred polythiol curing agents of this invention have one of the structures:

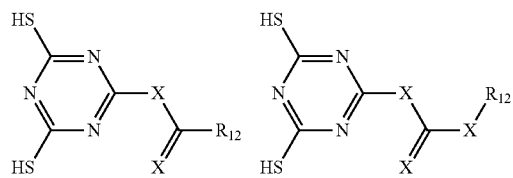

Wherein each X independently from each other is selected from the group of O, S, NH, NR$_{12}$ and R$_{12}$ independently is a monovalent organic radical.

Preferred R$_{12}$ is selected from the group consisting of a linear or branched alkyl group, an alkenyl group, an alkynyl group, a hydroxyalkyl group, an arylalkyl group, an alkylaryl group, and an alkoxylaryl group.

Other preferred polythiol curing agents of this invention have structure:

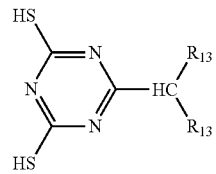

wherein R$_{13}$ independently from each other is a monovalent organic radical. Preferred R$_{13}$ are selected from the group consisting of hydrogen, a linear or branched alkyl group, an alkenyl group, an alkynyl group, a hydroxyalkyl group, an arylalkyl group, an alkylaryl group, and an alkoxylaryl group.

Other preferred polythiol curing agents of this invention have structure:

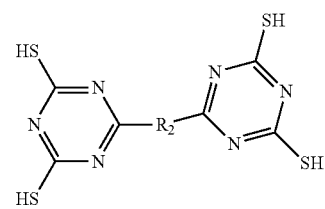

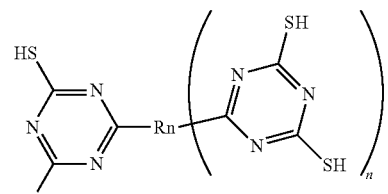

Wherein R$_2$ is selected from the group: —S—, —S—S—, —NH—, —NR$_3$—, —O—, —R$_4$—, —S—R$_4$—S—, —O—R$_4$—O—, —NH—R$_4$—NH—, —NR$_3$—R$_4$—NH—, —NR$_3$—R$_4$—NR$_3$—, —S—R$_4$—O—, -, —S—R$_4$—NH—, —O—R$_4$—NH—, -S-R$_4$—NR$_3$—, —O—R$_4$—NR$_3$—, wherein R$_4$ is a divalent organic radical as defined herein; and Rn is a multivalent organic radical. R$_1$, R$_2$, R$_3$, R$_4$, R$_n$, may be oligomeric or polymeric in nature, i.e. may contain repeating units of monomers such as glycols, ethylene glycol, propylene glycol, ethers, fluoroethers, olefins, fluoroolefines, acrylates and methacrylates, vinyl compounds, alkynes, esters, amino acids, lactones and lactames, polyols, urethanes, epoxies, hydroxacids, dienes, polyenes, chloroolefines, diols, diamines, polyamines. R$_1$, R$_2$, R$_3$, R$_4$, R$_n$, may optionally be substituted with a functional group or another organic radical as defined herein.

Preferred polythiol curing agents of this invention are a liquid, a viscous liquid, or a waxy solid at room temperature and have a viscosity lower than 100,000 cP at 50 C In another embodiment the preferred polythiol curing agents exist in different tautomeric forms that are in equilibrium with each other when is solution. Scheme 2 shows examples of such preferred polythiols for Structure A of Scheme 1 and Scheme 3 shows examples of examples of such preferred polythiols for Structure B of Scheme 1.

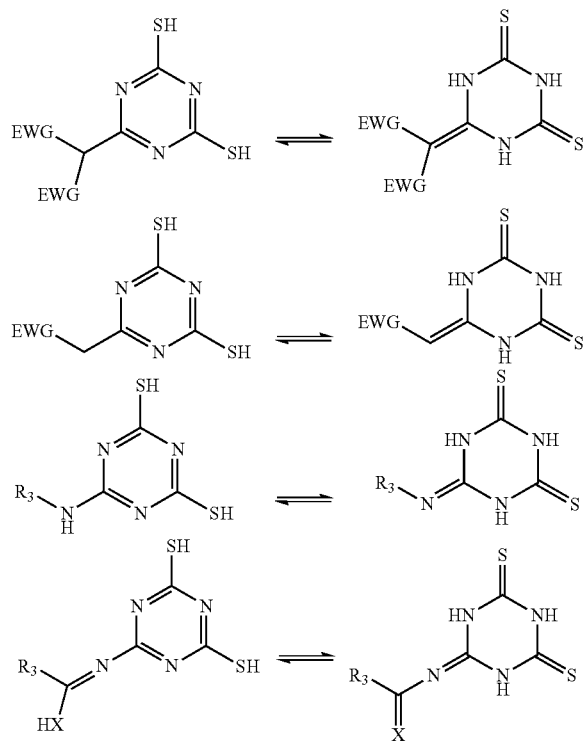

Scheme 2. Structures of preferred polythiols A that exist in different tautomeric forms that are in equilibrium with each other when is solution. EWG is an electron withdrawing group, which is a well-known definition in the art. EWGs include but are not limited to alkyl carbonyl, acyl, alkoxy carbonyl, carboxylic acid carboxylate anion, and cyano. X is an heteroatom such as N, S, O, P.

An epoxide, or oxirane, is a cyclic ether with three atoms in the ring, 2 carbon atoms and one oxygen atom. Epoxide groups of this invention include 1,2-epoxides (cis or trans), or terminal epoxides with structures:

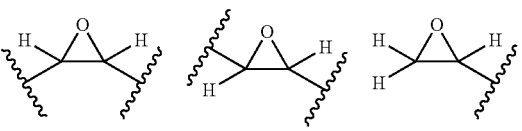

A polyepoxide, or epoxy resin, is a compound or a mixture of compounds with an average number of epoxide groups per molecule higher than 1, and preferably higher than 1.5. Preferred polyepoxides have two or more 1,2-epoxide groups. Polyepoxides may be small molecules or polymeric compounds, wherein the epoxide groups terminate the polymer chain or are pendant groups along the polymer chain. A polyepoxide may contain a mixture of one or more small molecules (non-polymeric epoxides) and one or more polymeric products. A polyepoxide mixture may optionally further comprise one or more compounds having a single epoxide per molecule (mono-epoxides). Typically this low-viscosity single-epoxide-per-molecule component is used to lower the viscosity of the mixture and does not contribute to the degree of cross-linking during cure, and such species are sometimes designated a reactive diluent. Examples of reactive diluents having a single epoxy group include, among others, aromatic glycidyl ethers, e.g., phenyl glycidyl ether, benzyl glycidyl ether, alkylphenyl glycidyl ether, cresyl glycidyl ether; or aliphatic glycidyl ethers (e.g., 2-ethylhexyl glycidyl ether, butyl glycidyl ether, C8-C10 aliphatic glycidyl ether, and C12-C14 aliphatic glycidyl ether).

The epoxide equivalent weight of an epoxy resin is the weight of polyepoxide in grams which contains one gram-equivalent of epoxide groups.

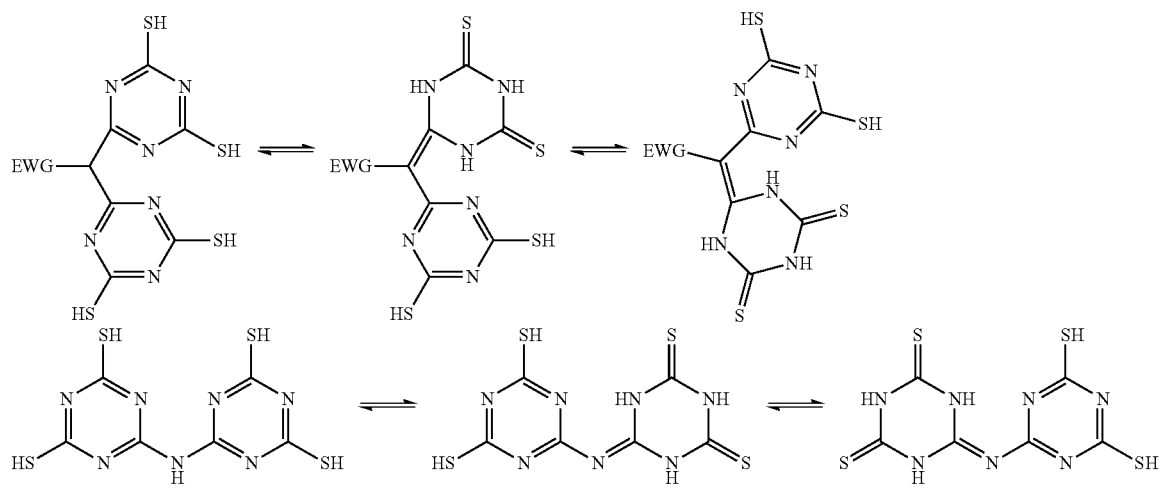

Scheme 3. Structures of preferred polythiols B that exist in different tautomeric forms that are in equilibrium with each other when is solution. EWG is an electron withdrawing group, which is a well-known definition in the art. EWGs include but are not limited to alkyl carbonyl, acyl, alkoxy carbonyl, carboxylic acid carboxylate anion, and cyano. X is an heteroatom such as N, S, O, P.

An isocyanate group is an organic functional group containing a nitrogen atom, an oxygen atom and a carbon atom bonded by double bonds and represented by the structure —N=C=O. A polyisocyanate, or isocyanate resin is a compound or a mixture of compounds with an average number of isocyanate groups per molecule higher than 1, and preferably higher than 1.5. Preferred polyisocyanates have two or more isocyanate groups. Polyisocyanates may be small molecules or polymeric compounds, wherein the isocyanate groups terminate the polymer chain or are pendant groups along the polymer chain. Polyisocyanates may contain a mixture of one or more small molecules (non-polymeric epoxides) and one or more polymeric products. A polyisocyanate mixture may optionally further comprise one or more compounds having a single isocyanate per molecule (mono-isocyanate). Typically this low-viscosity mono-isocyanate component is used to lower the viscosity of the mixture and does not contribute to the degree of cross-linking during cure, and such species are sometimes designated a reactive diluent.

The following are non-limiting examples of the invention.

EXAMPLE 1

Preparation of a Mixture Composition Containing a Compound Having Structure Type a in FIG. 1: Reaction of Glycidyl Phenyl Ether with 2,4,6-Trimercaptotriazine Under the Catalysis of 2,4,6-Tri(Dimethylaminomethyl) Phenol 2,4,6-trimercaptotriazine (1.5 gm, 0.008 mol, Taicros TMT, Evonik Degussa) was dissolved in tetrahydrofuran (THF, 20 ml). Glycidyl phenyl ether (1.39 gm, 0.009 mol) was added and allowed to stir several minutes. In a separate flask, 2,4,6-Tri(dimethylaminomethyl) phenol (0.04 gm, 0.0002 mol, Ancamine K54, Air Products and Chemicals) was dissolved in THF (5 ml) and added to reaction flask. The mixture was allowed to stir overnight at room temperature. The following day the solvent was removed by rotary vacuum and the product dried under Schlenk line vacuum. FT-IR and 1H-NMR analysis of the product indicated it was a mixture of unreacted TMT and the product of the reaction of TMT with Heloxy 63 followed by oligomerixation of a few Heloxy 63 units as an exemplary structure shown below.

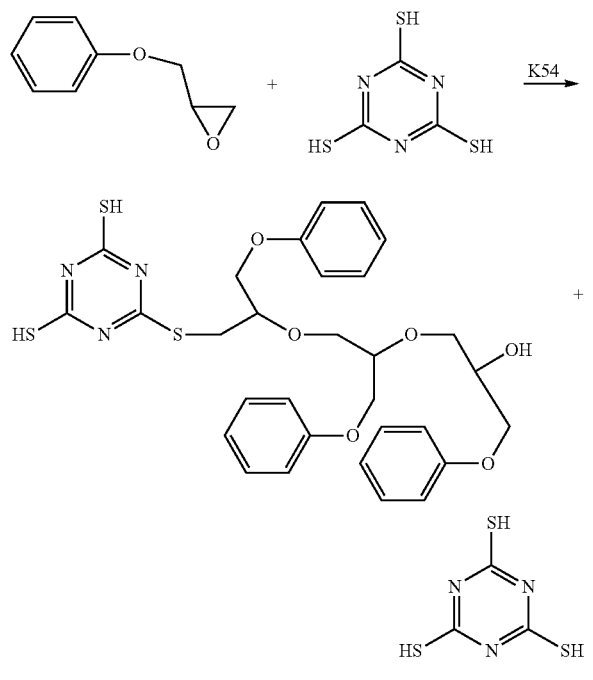

EXAMPLE 2

Preparation of a Mixture Composition Containing a Compound Having Structure Type a in FIG. 1: Reaction of Glycidyl Phenyl Ether with 2,4,6-Trimercaptotriazine Under the Catalysis of 2,2,6,6-Tetramethylpiperidine (TMP)

2,4,6-trimercaptotriazine (1.5 gm, 0.008 mol, Taicros TMT, Evonik Degussa) was dissolved in tetrahydrofurane (THF, 20 ml). Glycidyl phenyl ether (1.39 gm, 0.009 mol, Sigma Aldrich) was added and allowed to stir several minutes. In a separate flask, 2,2,6,6-tetramethylpiperidine (0.04 gm, Sigma Aldrich) was dissolved in THF (5 ml) and added to reaction flask. The mixture was allowed to stir overnight at room temperature. The following day the solvent was removed by rotary vacuum and the product dried under Schlenk line vacuum. FT-IR and 1H-NMR analysis of the product indicated it was mostly the desired product as shown below

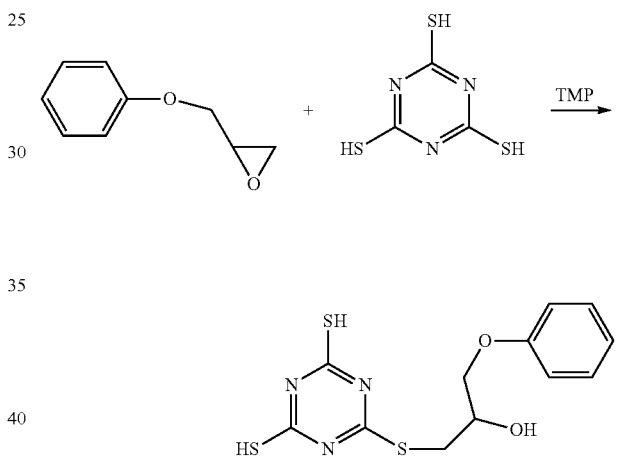

EXAMPLE 3

Preparation of a Mixture Composition Containing a Compound Having Structure Type a in FIG. 1: Reaction of 2-Ethylhexyl Glycidyl Ether with 2,4,6-Trimercaptotriazine Under the Catalysis of 2,2,6,6-Tetramethylpiperidine (TMP)

2,4,6-trimercaptotriazine (1.5 gm, 0.008 mol, Taicros TMT, Evonik Degussa) was dissolved in tetrahydrofuran (THF, 20 ml). 2-Ethylhexyl glycidyl ether (1.98 grams, 0.009 mol, Heloxy 116, Momentive Specialty Chemicals) was added and allowed to stir several minutes. In a separate flask, 2,2,6,6-tetramethylpiperidine (0.04 gm, Sigma Aldrich) was dissolved in THF (5 ml) and added to reaction flask. The mixture was allowed to stir overnight at room temperature. The following day the solvent was removed by rotary vacuum and the product dried under Schlenk line vacuum. The product was a yellow, viscous material. FT-IR and 1H-NMR analysis of the product indicated it was a mixture containing the desired product.

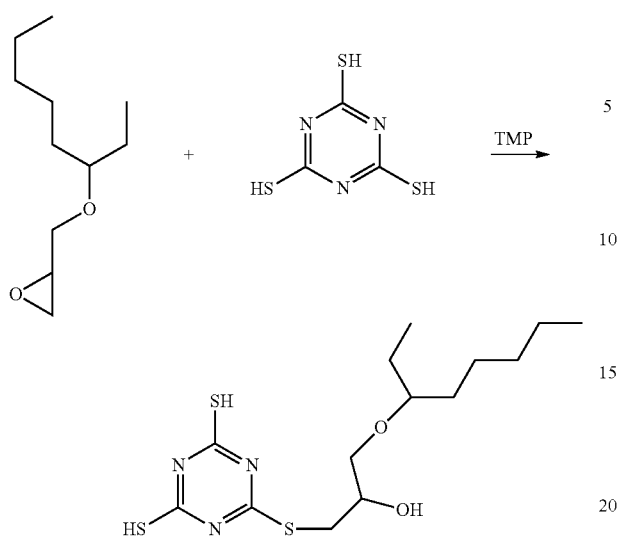

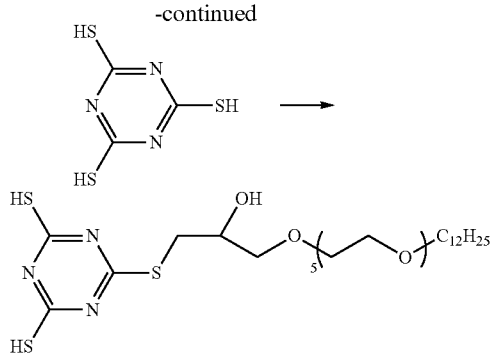

EXAMPLE 4

Preparation of a Mixture Composition Containing a Compound Having Structure Type A in FIG. 1: Reaction of Alkyl ($C_{12}$-$C_{14}$) Glycidyl Ether with 2,4,6-Trimercaptotriazine Under the Catalysis of 2,2,6,6-Tetramethylpiperidine (TMP)

2,4,6-trimercaptotriazine (1.5 gm, 0.008 mol, Taicros TMT, Evonik Degussa) was dissolved in tetrahydrofurane (THF, 20 ml). Alkyl (C12-C14) glycidyl ether (0.009 mol, GNS SG8008 reactive diluet, Dow) was added and allowed to stir several minutes. In a separate flask, 2,2,6,6-tetramethylpiperidine (0.04 gm, Sigma Aldrich) was dissolved in THF (5 ml) and added to reaction flask. The mixture was allowed to stir overnight at room temperature. The following day the solvent was removed by rotary vacuum and the product dried under Schlenk line vacuum. The product was a yellow, viscous material.

EXAMPLE 5

Reaction of C12 Terminated PEG Glycidyl Ether with 2,4,6-trimercaptotriazine Under the Catalysis of 2,2,6,6-tetramethylpiperidine (TMP)

2,4,6-trimercaptotriazine (3.4 gm, 0.019 mol, Taicros TMT, Evonik Degussa) was dissolved in tetrahydrofurane (THF, 20 ml). C12 terminated PEG glycidyl ether (Denacol Ex-171, Nagase Corporation, 8.156 g, 9.37 mmol) was added and allowed to stir several minutes. In a separate flask, 2,2,6, 6-tetramethylpiperidine (0.04 gm, Sigma Aldrich) was dissolved in THF (5 ml) and added to reaction flask. The mixture was allowed to stir overnight at room temperature. The following day the solvent was removed by rotary vacuum and the product dried under Schlenk line vacuum. The product was a light yellow, viscous liquid.

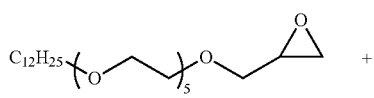

EXAMPLE 6

Reaction of 2-ethylhexyl isocyanate with 2,4,6-trimercaptotriazine 2,4,6-trimercaptotriazine (1.5 gm, 0.008 mol, Taicros TMT, Evonik Degussa) was dissolved in dichloromethane (20 ml). 2-Ethylhexyl isocyanate (0.009 mol, Sigma-Aldrich) was added together with a drop of dibutyltin dilaurate. The mixture was allowed to stir overnight at room temperature. The following day the solvent was removed by rotary vacuum and the product dried under Schlenk line vacuum. The product was a yellow, viscous material.

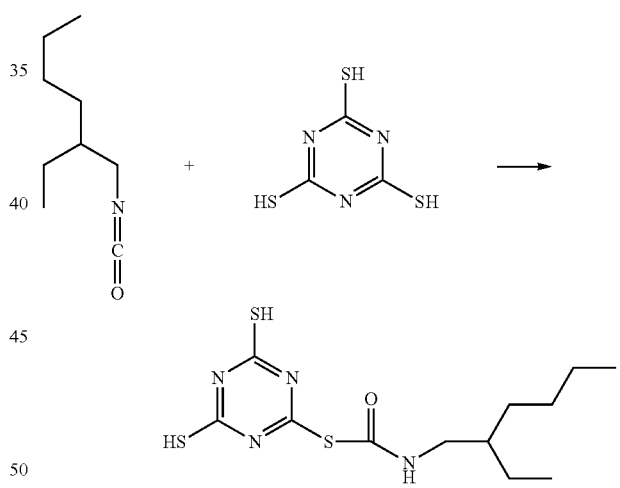

EXAMPLE 7

Reaction of oleoyl chloride with 2,4,6-trimercaptotriazine 2,4,6-trimercaptotriazine (1.5 gm, 0.008 mol, Taicros TMT, Evonik Degussa) was dissolved in chloroform (20 ml). Oleoyl chloride (0.009 mol, Sigma-Aldrich) was added together with 5% 4-dimethylamino pyridine (DMAP). The mixture was refluxed overnight. The following day the organic phase was diluted with dichloromethane, extracted with brine until pH=7, dried and solvent was removed by rotary vacuum. The product was a pale yellow viscous liquid.

EXAMPLE 8

Synthesis of 2 tert-butoxy-4,6-dimercaptotriazine

To a stirred solution of t-butyl-alcohol (294 μL, 3.08 mmol) in anhydrous hexane (2 mL) under argon at room temperature was added dropwise n-butyllithium (2.37 mL, 3.08 mmol, 1.3 M). The above mixture was added dropwise via cannula to a stirred solution of cyanuric chloride (567.5 mg, 3.08 mmol) in anhydrous THF (20 mL) under argon at room temperature. After 20 min Sodium hydrosulfide (9 mmol) was added. After 2.5 days the mixture was extracted with CH2Cl2, the combined organic layers were dried (MgSO4), filtered, evaporated to dryness and purified.

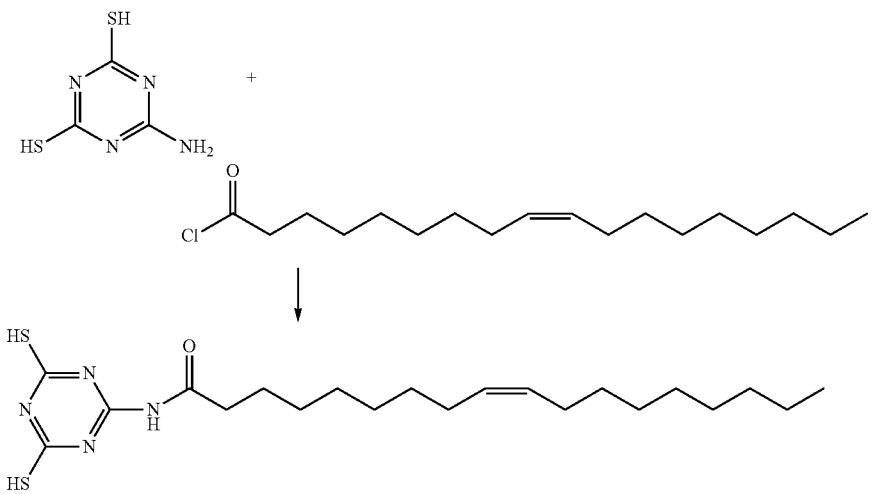

EXAMPLE 9

Reaction of 2-Amino-1,3,5-triazine-4,6-dithiol with oleoyl chloride

2-Amino-1,3,5-triazine-4,6-dithiol was suspended in a water solution of sodium dodecyl sulfate (SDS, 0.1 wt %). Excess oleoyl chloride was also suspended in a cold water solution of sodium dodecyl sulfate (SDS, 0.1 wt %). The two suspensions were mixed together and stirred at room temperature for 1 hr. Spectroscopy of the purified product indicated preferential acylation at the amino group over the thiol group.

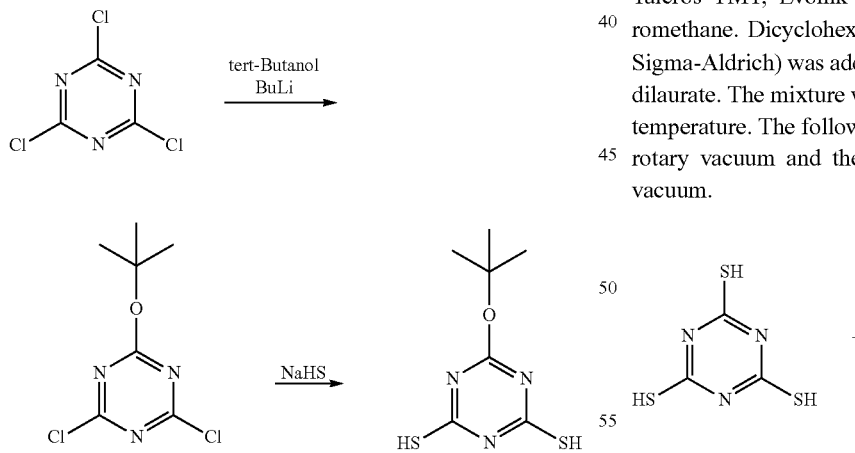

EXAMPLE 10

Preparation of a Mixture Composition Containing a Compound Having Structure Type B in FIG. 1: Reaction of with 2,4,6-trimercaptotriazine with Dicyclohexylmethane-4,4'-diisocyanate A four molar excess of 2,4,6-trimercaptotriazine (4 mol, Taicros TMT, Evonik Degussa) was dissolved in dichloromethane. Dicyclohexylmethane-4,4'-diisocyanate (1 mol, Sigma-Aldrich) was added together with a drop of dibutyltin dilaurate. The mixture was allowed to stir overnight at room temperature. The following day the solvent was removed by rotary vacuum and the product dried under Schlenk line vacuum.

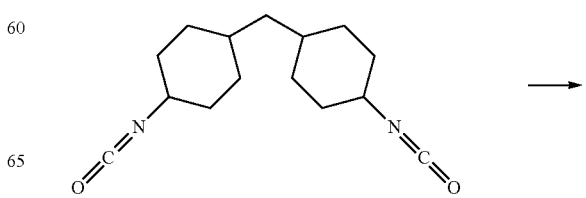

-continued

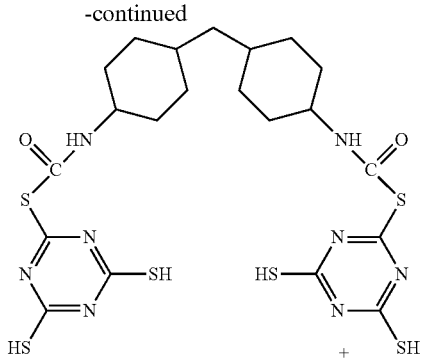

EXAMPLE 11

Reaction of neopentylglycol diglycidyl ether with 2,4,6-trimercaptotriazine Under the Catalysis of 2,2,6,6-tetramethylpiperidine (TMP)

2,4,6-trimercaptotriazine (6 gm, 0.032 mol, Taicros TMT, Evonik Degussa) was dissolved in tetrahydrofurane (THF, 80 ml). Noepentylglycol diglycidyl ether (2.16 gm, 0.009 mol, Heloxy 68, Momentive Specialty Chemicals) was added and allowed to stir several minutes. In a separate flask, 2,2,6,6-tetramethylpiperidine (0.04 gm, Sigma Aldrich) was dissolved in THF (5 ml) and added to reaction flask. The mixture was allowed to stir overnight at room temperature. The following day the solvent was removed by rotary vacuum and the product dried under Schlenk line vacuum.

EXAMPLE 12

Reaction of Poly(ethylene Glycol) diglycidyl ether (Mn=500) with 2,4,6-trimercaptotriazine Under the catalysis of 2,2,6,6-tetramethylpiperidine (TMP)

2,4,6-trimercaptotriazine (6 gm, 0.032 mol, Taicros TMT, Evonik Degussa) was dissolved in tetrahydrofurane (THF, 80 ml). Polyethylene glycol diglycidyl ether (4.5 gm, 0.009 mol, Sigma Aldrich) was added and allowed to stir several minutes. In a separate flask, 2,2,6,6-tetramethylpiperidine (0.04 gm, Sigma Aldrich) was dissolved in THF (5 ml) and added to reaction flask. The mixture was allowed to stir overnight at room temperature. The following day the solvent was removed by rotary vacuum and the product dried under Schlenk line vacuum.

EXAMPLE 13

Reaction of Poly(propylene Glycol) diglycidyl ether (Mn=640) with 2,4,6-trimercaptotriazine Under the catalysis of 2,2,6,6-tetramethylpiperidine (TMP)

2,4,6-trimercaptotriazine (6 grams, Taicros TMT, Evonik Degussa) was dissolved in tetrahydrofurane (THF, 80 ml). Poly(propylene glycol) diglycidyl ether (Mn=640) (6.12 grams, Sigma Aldrich) was added and allowed to stir several minutes. In a separate flask, 2,2,6,6-tetramethylpiperidine (0.04 gm, Sigma Aldrich) was dissolved in THF (5 ml) and added to reaction flask. The mixture was allowed to stir overnight at room temperature. The following day the solvent was removed by rotary vacuum and the product dried under Schlenk line vacuum

EXAMPLE 14

Synthesis of Bis(dimercaptotrazine) 2-ethylhexyl amine

Cyanuric chloride (2.128 mg) was dissolved in anhydrous THF at room temperature. Diisopropylethylamine (0.60 mL, 3.46 mmol) and 2-ethylhexyl amine (3.17 mmol) were added and the mixture was stirred for 2.5 days at room temperature. Sodium hydrosulfide (36 mmol) was added. After 2.5 days the mixture was extracted with CH2Cl2, the combined organic layers were dried (MgSO4), filtered, evaporated to dryness and purified.

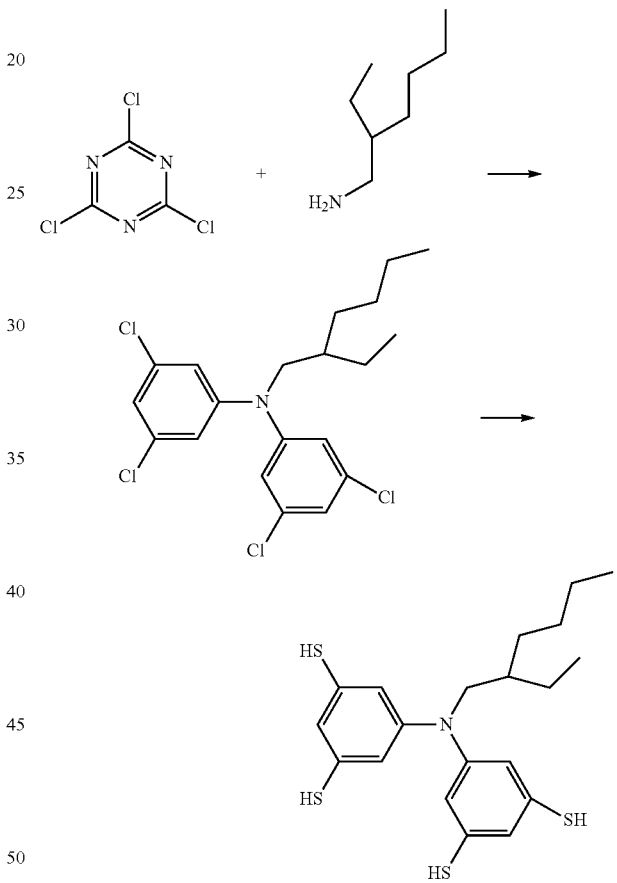

EXAMPLE 15

Preparation of Tautomer-Forming Compound

Cyanuric chloride (500 mg) was dissolved in anhydrous THF at room temperature. Diisopropylethylamine (0.60 mL, 3.46 mmol) and 2-ethylhexyl acetoacetate (3.17 mmol) were added and the mixture was stirred for 2.5 days at room temperature. Sodium hydrosulfide (8 mmol) was added. After 2.5 days the mixture was extracted with CH2Cl2, the combined organic layers were dried (MgSO4), filtered, evaporated to dryness and purified.

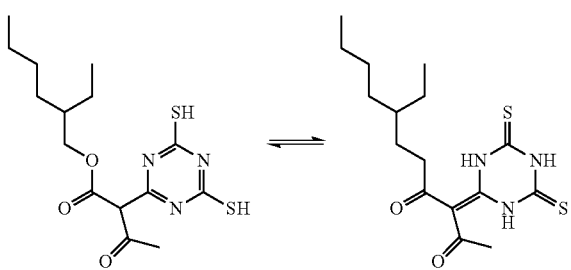 [SMILES: CCCCC(CC)COC(=O)C(C(C)=O)c1nc(S)nc(S)n1 ; CCCCC(CC)CCC(=O)C(C(C)=O)=C1NC(=S)NC(=S)N1]

EXAMPLE 16

Method of Making a Coating Using a Compound of the Type in FIG. 1 (Left Side) Combined with an Epoxy Compound Bisphenol A (20 g, EPON 824, Momentive) was mixed with a high shear mixer with the product of Example 3 (14 g) and 1.7 g of 2,4,6-tris(dimethylaminomethyl)phenol Ancamine K54, Air Product and Chemicals). The mixture was spread in a 1/16 inch thick layer on a metal plate and allowed to cure overnight to form a cured epoxy coating.

What is claimed is:

1. A polythiol comprising the chemical structure:

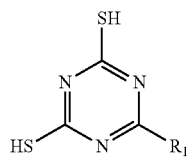

wherein $R_1$ is selected from the group consisting of A), B), C), D), E), F) and G):

A)
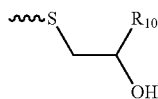

B)
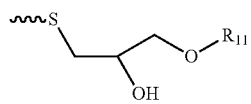

C)
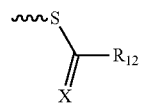

D)
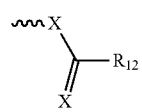

E)
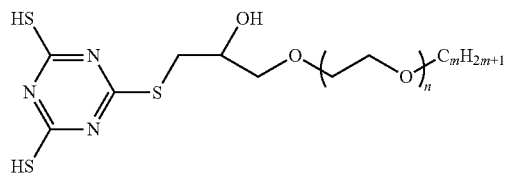

F)

G)

wherein, X is selected from the group consisting of O, S, NH and NR, wherein R is a monovalent organic radical; and wherein $R_{10}$, $R_{11}$, $R_{12}$, and $R_{13}$ is an oligomer comprising repeating units selected from the group consisting of glycols, ethylene glycol, propylene glycol, ethers, fluoroethers, olefins, fluoroolefins, acrylates, methacrylates, vinyl compounds, alkynes, esters, amino acids, lactones, lactames, polyols, urethanes, epoxies, hydroxacids, dienes, polyenes, chloroolefins, diols, diammines, and polyamines.

2. The polythiol of claim 1, wherein the oligomer is terminated by the group consisting of a hydrogen, a linear or branched alkyl group, an alkenyl group, an alkynyl group, a hydroxyalkyl group, an arylalkyl group, an alkylaryl group, and an alkoxyaryl group, an acyl group, a thioacyl group, alkylamino carbonyl group, an alkylaminothiocarbonyl group, an alkoxythiocarbonyl group, and an alkoxycarbonyl group.

3. The polythiol of claim 1 comprising the structure:

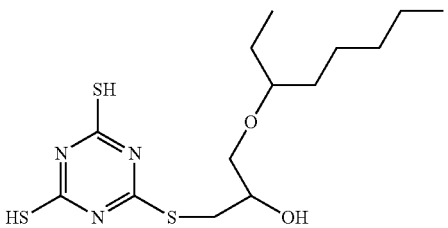

wherein n is an integer number from 2 to 30 and m is an integer number from 1 to 20.

4. The polythiol of claim 1 comprising the structure:

5. A polythiol as in any one of claim 1, 2, or 3 which is a liquid, a waxy solid or a semi-solid at 22° C.

6. A polythiol as in any one of claim 1, 2, or 3 which has a viscosity lower than 100,000 cP at 50° C.

* * * * *